US009309166B2

(12) United States Patent
Visagie et al.

(10) Patent No.: US 9,309,166 B2
(45) Date of Patent: Apr. 12, 2016

(54) CATALYSTS

(71) Applicant: SASOL TECHNOLOGY (PROPRIETARY) LIMITED, Rosebank (ZA)

(72) Inventors: Jacobus Lucas Visagie, Sasolburg (ZA); Tanja Allers, Frankenthal (DE); Frederik Marie Paul Rafael Van Laar, DH Maarssen (NL); Frederik Borninkhof, DC Ijsselstein (NL); Jana Heloise Taljaard, Vaalpark Sasolburg (ZA); Rita Meyer, Vereeniging (ZA)

(73) Assignee: SASOL TECHNOLOGY (PROPRIETARY) LIMITED, Johannesburg (ZA)

( * ) Notice: Subject to any disclaimer, the term of this patent is extended or adjusted under 35 U.S.C. 154(b) by 0 days.

(21) Appl. No.: 14/364,722

(22) PCT Filed: Nov. 30, 2012

(86) PCT No.: PCT/IB2012/056847
§ 371 (c)(1),
(2) Date: Jun. 12, 2014

(87) PCT Pub. No.: WO2013/088290
PCT Pub. Date: Jun. 20, 2013

(65) Prior Publication Data
US 2015/0057378 A1 Feb. 26, 2015

(30) Foreign Application Priority Data

Dec. 14, 2011 (ZA) .................................. 2011/09220

(51) Int. Cl.
| | |
|---|---|
| *B01J 21/08* | (2006.01) |
| *C07C 1/04* | (2006.01) |
| *B01J 37/02* | (2006.01) |
| *B01J 21/12* | (2006.01) |
| *B01J 23/02* | (2006.01) |
| *B01J 23/06* | (2006.01) |
| *B01J 23/10* | (2006.01) |
| *B01J 23/12* | (2006.01) |
| *B01J 23/20* | (2006.01) |
| *B01J 23/22* | (2006.01) |
| *B01J 23/30* | (2006.01) |
| *B01J 23/34* | (2006.01) |
| *B01J 23/72* | (2006.01) |
| *B01J 23/745* | (2006.01) |
| *B01J 23/75* | (2006.01) |
| *B01J 23/755* | (2006.01) |

(Continued)

(52) U.S. Cl.
CPC .............. *C07C 1/0445* (2013.01); *B01J 21/063* (2013.01); *B01J 21/066* (2013.01); *B01J 21/08* (2013.01); *B01J 21/12* (2013.01); *B01J 23/02* (2013.01); *B01J 23/06* (2013.01); *B01J 23/10* (2013.01); *B01J 23/12* (2013.01); *B01J 23/20* (2013.01); *B01J 23/22* (2013.01); *B01J 23/30* (2013.01); *B01J 23/34* (2013.01); *B01J 23/72* (2013.01); *B01J 23/745* (2013.01); *B01J 23/75* (2013.01); *B01J 23/755* (2013.01); *B01J 23/8913* (2013.01); *B01J 31/0274* (2013.01); *B01J 35/002* (2013.01); *B01J 37/0203* (2013.01); *B01J 37/0205* (2013.01); *B01J 37/0207* (2013.01); *B01J 37/0209* (2013.01); *C10G 2/33* (2013.01); *C10G 2/331* (2013.01); *C10G 2/332* (2013.01); *C10G 2/333* (2013.01)

(58) Field of Classification Search
CPC ......... B01J 21/08; B01J 21/066; B01J 21/063
See application file for complete search history.

(56) References Cited

U.S. PATENT DOCUMENTS

| | | | |
|---|---|---|---|
| 4,086,261 A | | 4/1978 | Mitchell et al. |
| 5,169,821 A | * | 12/1992 | Soled et al. .................... 502/242 |

(Continued)

FOREIGN PATENT DOCUMENTS

| | | |
|---|---|---|
| WO | 99/42214 | 8/1999 |
| WO | 00/20116 | 4/2000 |

(Continued)

OTHER PUBLICATIONS

Sato, et al., "Structural and Catalytic Properties of Silica-Coated Alumina", "The Chemical Society of Japan", pp. 649-655, vol. 79, No. 4, Publisher: Bull. Chem. Soc. Jpn. (2006).

(Continued)

*Primary Examiner* — Sudhakar Katakam
(74) *Attorney, Agent, or Firm* — Fellers, Snider, Blankenship, Bailey & Tippens, P.C.

(57) ABSTRACT

A method of preparing a modified catalyst support comprises contacting a catalyst support material with a modifying component precursor in an impregnating liquid medium. The impregnating liquid medium comprises a mixture of water and an organic liquid solvent for the modifying component precursor. The mixture contains less than 17% by volume water based on the total volume of the impregnating liquid medium. The modifying component precursor comprises a compound of a modifying component selected from the group consisting of Si, Zr, Co, Ti, Cu, Zn, Mn, Ba, Ni, Al, Fe, V, Hf, Th, Ce, Ta, W, La and mixtures of two or more thereof. A modifying component containing catalyst support material is thus obtained. Optionally, the modifying component containing catalyst support material is calcined at a temperature above 100° C. to obtain a modified catalyst support.

9 Claims, 4 Drawing Sheets

(51) Int. Cl.
*B01J 23/89* (2006.01)
*B01J 31/02* (2006.01)
*B01J 35/00* (2006.01)
*C10G 2/00* (2006.01)
*B01J 21/06* (2006.01)

(56) References Cited

U.S. PATENT DOCUMENTS

| | | |
|---|---|---|
| 7,365,040 B2 | 4/2008 | Van Berge et al. |
| 2011/0230574 A1 | 9/2011 | Li et al. |

FOREIGN PATENT DOCUMENTS

| | | |
|---|---|---|
| WO | 02/07883 A2 | 1/2002 |
| WO | 03/012008 A2 | 2/2003 |
| WO | 2005058493 A1 | 6/2005 |
| WO | 2009/049280 A2 | 4/2009 |
| WO | 2011089411 A1 | 7/2011 |

OTHER PUBLICATIONS

Wang, et al., "Silica Coating on Ultrafine a-alumina Particles", Publisher: Elsevier, Materials Science and Engineering A 395 (2005) 148-152.

* cited by examiner

CATALYSTS

FIELD OF THE INVENTION

THIS INVENTION relates to catalysts. More particularly, it relates to a method of preparing a modified catalyst support, to a method of preparing a catalyst precursor, to a method of preparing a catalyst, and to a hydrocarbon synthesis process employing the resultant catalyst.

BACKGROUND ART

Hydrocarbon synthesis from hydrogen and carbon monoxide in the presence of a Fischer-Tropsch catalyst is commonly known as Fischer-Tropsch (FT) synthesis. FT synthesis forms part of gas-to-liquids, coal-to-liquids, and biomass-to-liquids processes in which natural gas, coal, and biomass respectively are usually converted by means of a three step process into liquid hydrocarbons. The three process steps are normally (i) production of synthesis gas (or 'syngas') comprising a mixture of hydrogen and carbon monoxide from natural gas, coal, or biomass respectively, (ii) conversion of the syngas into a waxy hydrocarbons or syncrude by means of FT synthesis, and (iii) a hydrocracking or hydrotreating step to convert the waxy syncrude into liquid transportation fuels such as diesel, petrol, jet fuel, as well as naphtha.

During the FT synthesis described in step (ii) above the syngas in the form of CO and $H_2$ is contacted with a FT synthesis catalyst under FT synthesis conditions to produce the waxy hydrocarbons. One type of catalyst which is often used in low temperature FT (LTFT) synthesis comprises an active catalyst component such as Co on a catalyst support such as alumina, silica, titania, magnesia or the like.

Contamination of the waxy hydrocarbon product produced during FT synthesis with ultra fine particulate matter derived from the support such as alumina, and the active catalyst component such as Co, was experienced. This resulted in loss of the expensive active catalyst component as well as fouling of the downstream processes described in (iii) above with the support and active catalyst component ultra fine particles. It is believed that this wax product contamination is as a result of one or both of: (a) Catalyst support dissolution during aqueous impregnation of the catalyst support with the active catalyst component (during preparation of the catalyst) which may result in precipitation and coating of the bulk support material with a physically bonded amorphous layer of the support material whereon the active catalyst component is deposited. This amorphous layer is insufficiently anchored and results in dislodgement of and washing out of active catalyst component rich ultra fine particles during FT synthesis; and (b) The FT synthesis catalyst is susceptible to hydrothermal attack that is inherent to realistic FT synthesis conditions. Such a hydrothermal attack on exposed and unprotected support material will result in contamination of the waxy hydrocarbon product with ultra fine particulate matter rich in the active catalyst component.

WO 99/42214, WO 02/07883, WO 03/012008 and U.S. Pat. No. 7,365,040 all disclose modification of a FT synthesis catalyst support with a modifying component to reduce the dissolution of the catalyst support in aqueous environment, including hydrothermal attack, thereby to reduce the negative effect of ultra fine particles rich in active catalyst component contaminating the waxy hydrocarbon product.

WO 99/42214, WO 02/07883, and U.S. Pat. No. 7,365,040 all disclose modification of a FT synthesis catalyst support by impregnation of the support with the modifying component carried in an organic solvent such as ethanol. Water is specifically avoided in order to avoid dissolution of the support in an aqueous environment during the support modification process.

WO 2009/049280 discloses modification of a catalyst support by impregnating the support with a modifying component carried in water. WO 2009/049280 is not limited to the preparation of FT catalysts and accordingly the problem associated with support dissolution in an aqueous medium does not play such an important role in that case. It should be noted that WO 2009/049280 discloses, on page 17, that when the use of water is compared to the use of anhydrous ethanol during impregnation of the support with the modifying component, a lower silicon content on the support is achieved when water is used. This is accordingly a disadvantage associated with water as an impregnating liquid medium.

Most surprisingly, it has now been found that when a certain mixture of water and an organic solvent was used to impregnate a modifying component onto a catalyst support, it may result in a higher modifying component content being deposited on the support compared to when no water is used during impregnation. It thus resulted in better utilisation of the modifying component. This is contrary to what is expected from the teachings of WO 2009/049280 set out above, namely that the use of water instead of ethanol as an impregnating liquid medium resulted in lower usage of the modifying component. This higher usage of the modifying component resulted in a higher loading of the modifying component or alternatively less wastage of the modifying component. It is well known that a higher loading of the modifying component results in a lower solubility of the catalyst support in water. Surprisingly, when specified amounts of water were used in the impregnating liquid medium, it resulted in improved attrition resistance of the modified catalyst support compared to the use of only water (and in some cases of only ethanol) as the impregnating liquid medium.

DISCLOSURE OF THE INVENTION

According to a first aspect of the invention, there is provided a method of preparing a modified catalyst support, the method comprising contacting a catalyst support material with a modifying component precursor in an impregnating liquid medium wherein the impregnating liquid medium comprises a mixture of water and an organic liquid solvent for the modifying component precursor, which mixture contains less than 17% by volume water based on the total volume of the impregnating liquid medium, and the modifying component precursor comprises a compound of a modifying component selected from the group consisting of Si, Zr, Co, Ti, Cu, Zn, Mn, Ba, Ni, Al, Fe, V, Hf, Th, Ce, Ta, W, La and mixtures of two or more thereof, thereby to obtain a modifying component containing catalyst support material; and optionally, calcining the modifying component containing catalyst support material at a temperature above 100° C. to obtain a modified catalyst support.

It will be appreciated that, in one embodiment of the invention, no calcination above 100° C. of the modifying component containing catalyst support material takes place so that the non-calcined modifying component containing catalyst support material then constitutes the modified catalyst support. In other words, a non-calcined modified catalyst support is then produced.

In an alternative embodiment of the invention, calcination above 100° C. of the modifying component containing catalyst support material takes place to provide the modified catalyst support in the form of a calcined modified catalyst support.

According to a second aspect of the invention, there is provided a method of preparing a catalyst precursor, the method comprising contacting a catalyst support material with a modifying component precursor in an impregnating liquid medium wherein the impregnating liquid medium comprises a mixture of water and an organic liquid solvent for the modifying component precursor, which mixture contains less than 17% by volume water based on the total volume of the impregnating liquid medium, and the modifying component precursor comprises a compound of a modifying component selected from the group consisting of Si, Zr, Co, Ti, Cu, Zn, Mn, Ba, Ni, Al, Fe, V, Hf, Th, Ce, Ta, W, La and mixtures of two or more thereof, thereby to obtain a modifying component containing catalyst support material;

optionally, calcining the modifying component containing catalyst support material at a temperature above 100° C. to obtain a modified catalyst support; and introducing a precursor compound of an active catalyst component onto and/or into (i) the catalyst support material prior to contacting the catalyst support material with the modifying component precursor; (ii) the modifying component containing catalyst support material; and/or (iii) the modified catalyst support, thereby to obtain a catalyst precursor.

It will be appreciated that in one embodiment of the invention no calcination above 100° C. of the modifying component containing catalyst support material takes place so that the non-calcined modifying component containing catalyst support material then constitutes the modified catalyst support. In other words, a non-calcined modified catalyst support is then produced.

In an alternative and preferred embodiment of the invention, calcination above 100° C. of the modifying component containing catalyst support material takes place to provide the modified catalyst support in the form of a calcined modified catalyst support.

It will be appreciated that when the precursor compound of the active catalyst component is introduced onto and/or into the modified catalyst support it may be onto and/or into the non-calcined modified catalyst support or the calcined modified catalyst support. Preferably the active catalyst component is introduced onto and/or into the calcined modified catalyst support.

The Impregnating Liquid Medium

The impregnating liquid medium thus contains less than 17% by volume water. Preferably, however, the impregnating liquid medium contains less than 12% by volume water; preferably not more than 10% by volume water. Preferably, the impregnating liquid contains at least 0.4% by volume water, preferably more than 0.4% by volume water, preferably at least 2.5% by volume water, preferably at least 3% by volume water.

The organic liquid solvent may comprise a liquid organic compound which includes at least one heteroatom selected from oxygen or nitrogen. When the heteroatom is oxygen, it may be part of an oxygen containing group selected from an alcohol, a ketone, an aldehyde, an ether, an ester, a glycol, an acid (including an organic acid) and a mixture of two or more thereof. Preferably the oxygen containing liquid organic compound is an alcohol, and preferably it is C1 to C10 alcohol, preferably a C1 to C3 alcohol. Preferably the alcohol includes a single OH group and preferably the alcohol is ethanol. Alternatively the oxygen containing liquid organic compound may be selected from the group consisting of ethyl acetate and acetone. When the heteroatom is nitrogen, the nitrogen containing organic compound may be acetonitrile. The organic liquid solvent may comprise a mixture of organic compounds, preferably a mixture of organic compounds as described above.

In one embodiment of the invention, the organic liquid solvent may be a polar solvent. In one embodiment of the invention, the organic liquid solvent may have a boiling point of not more than 97° C., preferably not more than 80° C.

The Catalyst Support Material

The catalyst support material that is contacted with the modifying component precursor may be selected from the group consisting of a catalyst support precursor which is convertible to a catalyst support upon calcination thereof; and a catalyst support.

When the catalyst support material is a catalyst support precursor, it may be a compound which, upon calcination, converts to a catalyst support in the form of an oxide, preferably a metal oxide. Preferably, the metal oxide is an oxide of a metal selected from the group consisting of Al, Si, Ti, Mg, Zr and Zn. More particularly, the catalyst support precursor may then comprise an aluminium compound which converts to one or more aluminium oxides upon calcination. Preferably, the aluminium compound is $Al(OH)_3$, such as gibbsite and/or bayerite and/or AlO(OH), and more preferably it is boehmite. The catalyst support precursor may be shaped into particulate form after the introduction of the modifying component precursor onto and/or into the catalyst support precursor and before calcination thereof. The shaping may, for example, be carried out by means of spray drying. Prior to shaping the catalyst support precursor, it may be partially dried. The resulting shaped product may then be subject to the calcination above 400° C. This calcination preferably takes place prior to introducing the catalyst precursor compound onto and/or into the shaped product. In order to achieve a desired particle size distribution, classification may be performed on the shaped particulate product, using, for example, cyclones or sieves.

However, the catalyst support material is preferably a catalyst support. The catalyst support may then be any catalyst support suitable for supporting thereon the active catalyst component or a precursor compound of the active catalyst component. The catalyst support is preferably suitable for use as a support in a catalyst for synthesising hydrocarbons and/or oxygenates of hydrocarbons from at least hydrogen and carbon monoxide, particularly a Fischer-Tropsch (FT) synthesis catalyst. The FT synthesis catalyst may be for use in a process to be performed in a fixed bed reactor, slurry bed reactor or even a fixed fluidized bed reactor. Preferably, the process is to be performed in a three phase slurry bed FT synthesis reactor.

The catalyst support is usually a porous support, and preferably it is also preshaped. The porous support preferably has an average pore diameter from 8 to 50 nanometers, more preferably from 10 to 15 nanometers. The pre-shaped support may be a particulate support, preferably with an average particle size of from 1 to 500 micrometers, more preferably from 10 to 250 micrometers, and still more particularly from 45 to 200 micrometers.

The catalyst support may be selected from the group consisting of alumina in the form of one or more aluminium oxides; silica ($SiO_2$); titania ($TiO_2$); magnesia (MgO); zirconium oxide ($ZrO_2$), zinc oxide (ZnO); and mixtures thereof. Preferably, the support is selected from the group consisting of alumina in the form of one or more aluminium oxides and titania ($TiO_2$). More preferably, the support is alumina in the form of one or more aluminium oxides.

The one or more aluminium oxides may be selected from the group including (preferably consisting of) gamma alumina, theta alumina and a mixture of two or more thereof. Preferably the group includes, or, more preferably, consists of, gamma alumina, theta alumina and a mixture of gamma alumina and theta alumina. The aluminium oxide catalyst support may be that obtainable under the trademark Puralox, preferably Puralox SCCa 150, from SASOL Germany GmbH. Puralox SCCa 150 is a spray-dried aluminium oxide support consisting of a mixture of gamma and theta aluminium oxide.

The aluminium oxide may be a crystalline compound which can be represented by the formula $Al_2O_3.xH_2O$ where $0<x<1$. The term 'aluminium oxide' thus excludes $Al(OH)_3$, and $AlO(OH)$, but includes compounds such as gamma, delta and theta alumina.

The Modifying Component Precursor

The modifying component precursor may comprise an inorganic compound of the modifying component. Preferably however, the modifying component precursor includes one or more organic groups bound to the modifying component. Preferably one or more, but preferably all, organic groups are bound to the modifying component via an oxygen atom. Preferably all the groups bound to the modifying component are organic groups and preferably all said organic groups are bound to the modifying component via an oxygen atom.

In a preferred embodiment of the invention some, but preferably all, the organic groups are of the formula —(O)—R where R is an organic group. R may be an acyl, an aryl, an heteroaryl, a cyclic compound (including a heterocyclic compound) or a hydrocarbyl group, preferably a hydrocarbyl group, preferably an alkyl group, preferably an alkyl group with not more than ten carbon atoms, and preferably an alkyl group with not more than three carbon atoms. Alternatively, R may be of the formula —$OR^1$ where $R^1$ may be a hydrocarbyl group, preferably an alkyl group, preferably an alkyl group with not more than ten carbon atoms, and preferably an alkyl group with not more than three carbon atoms.

The modifying component may be selected from the group consisting of Si, Zr, Ti, Cu, Zn, Mn, Ba, Ni, Al, V, W, La and mixtures of two or more thereof.

Preferably the modifying component is selected from the group consisting of Si, Ti and Zr.

In a preferred embodiment of the invention, the modifying component is Si. Preferably the modifying component precursor is then an organic silicon compound, preferably of the formula $Si(OR)_4$ where R is an organic group. Preferably R is an alkyl or acyl group. Preferably the modifying component precursor is then tetra ethoxy silane (TEOS) or tetra methoxy silane (TMOS).

In another embodiment of the invention, the modifying component may be Zr. The modifying component precursor may then be an organic zirconium compound, preferably of the formula $Zr(OR)_4$ where R is an organic group. Preferably R is an alkyl or acyl group. Preferably the modifying component precursor is then a zirconium alkoxide, for example zirconium isopropoxide ($Zr(OCH(CH_3)_2)_4$.

In yet another embodiment of the invention, the modifying component may be Ti. The modifying component precursor may then be an organic titanium compound, preferably of the formula $Ti(OR)_4$ where R is an organic group. Preferably R is an alkyl or acyl group. Preferably the modifying component precursor is then a titanium alkoxide, for example titanium tetrabutoxide.

Contacting of the Catalyst Support Material with the Modifying Component Precursor By contacting the catalyst support material with the modifying component precursor in the impregnating liquid medium, the modifying component precursor is thus introduced into and/or onto the catalyst support material by means of impregnation. The impregnation may be incipient wetness impregnation, but preferably it is slurry phase impregnation.

The impregnation by means of the impregnating liquid medium is preferably carried out at a temperature above 25° C. The temperature may be at or near the boiling point of the impregnating liquid medium. The impregnation may be carried out for a period from 1 minute to 20 hours, preferably from 1 minute to 5 hours. The impregnation may be effected at atmospheric pressure.

After impregnation the excess impregnating liquid medium may be removed, preferably at sub-atmospheric conditions, preferably from 0.01 to 0.1 bar(a). The removal is preferably carried out at temperature above 25° C., preferably at or near the boiling point of the impregnating liquid medium.

During impregnation, sufficient impregnating liquid medium may thus be used to cause conditions of incipient wetness, alternatively conditions of slurry impregnation.

Optional Calcination of the Modifying Component Containing Catalyst Support Material This calcination, when employed, is thus effected at a temperature above 100° C., preferably at a temperature of at least 150° C. preferably at least 450° C. Where the modifying component is Si, the calcination is preferably not effected at a temperature above 550° C. The calcination may be for a period from 1 minute to 12 hours, preferably from 10 minutes to 4 hours.

The calcination may be effected in a non-reducing gas, preferably in an oxygen containing gas, preferably in air.

Preferably the calcination results in decomposition of the modifying component precursor. Preferably, during calcination the modifying component precursor is converted to an oxide of the modifying component.

Introducing the Precursor Compound of the Active Catalyst Component

The active catalyst component may be a known component active for hydrocarbon synthesis process (preferably a FT synthesis process), and may be selected from the group consisting of cobalt (Co), iron (Fe), nickel (Ni) and ruthenium (Ru). Cobalt (Co) is preferred.

The precursor compound may thus be any suitable compound of the active catalyst component. Preferably, it is an inorganic compound, more preferably an inorganic salt of the active catalyst component. The catalyst precursor compound may be cobalt nitrate, and particularly it may be $Co(NO_3)_2 \cdot 6H_2O$.

The precursor compound may be introduced by any suitable manner, but preferably it is by means of impregnation. Preferably, the modified catalyst support or the catalyst support material is impregnated with the catalyst precursor compound by forming a mixture of the precursor compound; a liquid carrier for the precursor compound; and the modified catalyst support or the catalyst support material.

The liquid carrier may comprise a solvent for the precursor compound and preferably the precursor compound is dissolved in the liquid carrier. The liquid carrier may be water.

The impregnation may be effected by any suitable impregnation method, including incipient wetness impregnation or slurry phase impregnation. Slurry phase impregnation is preferred. Preferably, the precursor compound is dissolved in the liquid carrier in order that the volume of the solution is greater than xy liter, which solution is then mixed with the modified catalyst support or the catalyst support material, and wherein x is the BET pore volume of the modified catalyst support or the catalyst support material in l/kg support, and y is the mass of modified catalyst support or catalyst support material to be impregnated in kg. Preferably the volume of the solution is greater than 1.5xy liter, and preferably it is about 2xy liter.

The impregnation may be carried out at sub-atmospheric pressure, preferably below 85 kPa(a), preferably at 20 kPa(a) and lower. Preferably the impregnation is also carried out at a temperature above 25° C. The impregnation temperature may be above 40° C., preferably above 60° C., but preferably not above 95° C.

The impregnation may be followed by partial drying of the impregnated support, preferably at a temperature above 25° C. The drying temperature may be above 40° C., preferably above 60° C., but preferably not above 95° C. Preferably the partial drying may be effected at sub-atmospheric conditions, preferably below 85 kPa(a), preferably at 20 kPa(a) or lower.

In one embodiment of the invention, the impregnation and partial drying of the modified catalyst support or the catalyst support material may be carried out using a procedure which includes a first step wherein the modified catalyst support or the catalyst support material is impregnated (preferably slurry impregnated) with the precursor compound at a temperature above 25° C., and at sub-atmospheric pressure, and the resultant product is dried; and at least one subsequent step wherein the resulting partially dried impregnated modified catalyst support or catalyst support material of the first step is subjected to treatment at a temperature above 25° C., and sub-atmospheric pressure such that the temperature of the subsequent step exceeds that in the first step and/or the sub-atmospheric pressure in the subsequent step is lower than that in the first step. This two step impregnation procedure may be as described in WO 00/20116, which is incorporated herein by reference.

A dopant capable of enhancing the reducibility of the active catalyst component may also be introduced onto and/or into the modified catalyst support or the catalyst support material. The dopant may be introduced during or after the introduction of the catalyst precursor compound onto and/or into the modified catalyst support or the catalyst support material. The dopant may be introduced as a dopant compound which is a compound of a metal selected from the group including palladium (Pd), platinum (Pt), ruthenium (Ru), rhenium (Re) and a mixture of two or more thereof. Preferably, the dopant compound is an inorganic salt, and it is preferably soluble in water. The mass proportion of the metal of the dopant to the active catalyst component metal may be in the ratio of 0.01:100 to 3:100.

The partially dried catalyst support with the catalyst precursor compound thereon and/or therein may be calcined. The calcination may be effected in order to decompose the catalyst precursor compound and/or causing it to react with oxygen. For example, cobalt nitrate may be converted into a compound selected from CPO, CoO(OH), $Co_3O_4$, $Co_2O_3$ or a mixture of two or more thereof.

The calcination may be carried out in any suitable manner such as in a rotary kiln, but preferably it is carried out in a fluidised bed reactor.

The calcination may be carried out in an inert atmosphere, but preferably it is carried out in the presence of oxygen, more preferably in air.

Preferably the calcination is carried out at a temperature above 95° C., more preferably above 120° C., still more preferably above 200° C., but preferably not above 400° C., more preferably not above 300° C. This is especially the case where Co is the active catalyst component.

The calcination may be carried out by using a heating rate and an air space velocity that comply with the following criteria:
 (i) when the heating rate is ≤1° C./min, the air space velocity is at least 0.76 $m_n^3$/(kg $Co(NO_3)_2.6H_2O$)/h; and
 (ii) when the heating rate is higher than 1° C./min, the air space velocity satisfies the relation:

$$\log(\text{space velocity}) \geq \log\ 0.76 + \frac{\log 20 - \log 0.76}{2}\log(\text{heating rate})$$

The above conditions for air space velocity and heating rate are especially applicable where Co is the active catalyst component.

The impregnation, the partial drying and calcination may be repeated to achieve higher loadings of the catalyst precursor compound on the catalyst support or the catalyst support material. In one embodiment of the invention, a first impregnation, drying and calcination procedure may be followed by a partial reduction procedure of the calcined material; and the partially reduced material may then be subjected to a further impregnation, drying and calcination procedure. The partial reduction procedure may be executed with a final temperature of between 100° C. and 300° C., especially in the case where Co is the active catalyst component.

In one embodiment of the invention, the catalyst precursor may be prepared by a method which includes, in a first preparation step, impregnating the modified catalyst support or the catalyst support material with an organic metal compound of the active catalyst component in a carrier liquid, at least partially drying the impregnated support or support material, and calcining the at least partially dried impregnated support or support material, to obtain a calcined intermediate; and in a second preparation step, impregnating the calcined intermediate from the first impregnation step, with an inorganic metal salt of the active catalyst component in a carrier liquid, at least partially drying the impregnated support, and calcining the at least partially dried impregnated support, to obtain the catalyst precursor. The organic metal compound may be an organic cobalt compound.

The catalyst precursor may have reduced dissolution in an aqueous environment, preferably an acidic aqueous environment.

Catalyst

According to a third aspect of the invention, there is provided a method of preparing a catalyst, which includes preparing a catalyst precursor using the method of the second aspect of the invention; and reducing the catalyst precursor, thereby activating the catalyst precursor and obtaining the catalyst. The reduction of the catalyst precursor preferably includes treating it with a reducing gas to activate it. Preferably, the reducing gas is hydrogen or a hydrogen containing gas. The hydrogen containing gas may consist of hydrogen and one or more inert gases which are inert in respect of the active catalyst. The hydrogen containing gas preferably contains at least 90 volume % hydrogen.

The reducing gas may be contacted with the catalyst precursor in any suitable manner. Preferably the catalyst precursor is provided in the form of a bed with the reducing gas being caused to flow through the bed of particles. The bed of particles may be a fixed bed, but preferably it is a fluidised bed and preferably the reducing gas acts as the fluidising medium for the bed of catalyst precursor particles.

The reduction may be carried out at a pressure from 0.6 to 1.5 bar(a), preferably from 0.8 to 1.3 bar(a). Alternatively the pressure may be from 1.5 bar(a) to 20 bar(a). Preferably, however, the pressure is at about atmospheric pressure.

The reduction is preferably carried out at a temperature in excess of 25° C. above that at which the catalyst precursor will be reduced to an active form. Preferably, the activation is carried out at a temperature above 150° C., and preferably below 600° C., especially where the active catalyst component is cobalt. Preferably the reduction is carried out at a temperature below 500° C., more preferably below 450° C.

During activation the temperature may be varied, and preferably it is increased to a maximum temperature as set out above.

The flow of the reducing gas through the catalyst bed is preferably controlled to ensure that contaminants produced during reduction are maintained at a sufficiently low level. The reducing gas may be recycled, and preferably the recycled reducing gas is treated to remove one or more contaminants produced during reduction. The contaminants may comprise one or more of water and ammonia.

The activation may be carried out in two or more steps during which one or both of the heating rate and the space velocity of the reducing gas is varied.

In one embodiment of the invention, the active catalyst may be coated by introducing a mixture of active catalyst particles and a coating medium in the form of molten organic substance, which is at a temperature $T_1$, and which sets or congeals at a lower temperature $T_2$ so that $T_2 < T_1$, into at least one mould; and at least partly submerging the mould in a cooling liquid, so as to cool the organic substance down to a temperature $T_3$, where $T_3 \leq T_2$.

During the activation the water partial pressure is preferably kept as low as possible, more preferably below 0.1 atmosphere. The hydrogen space velocity may be from 2 to 4 liters per hour per gram of catalyst.

Hydrocarbon Synthesis

According to a fourth aspect of the present invention, there is provided a hydrocarbon synthesis process which comprises preparing a catalyst using the process of the third aspect of the invention; and contacting hydrogen with carbon monoxide at a temperature above 100° C. and a pressure of at least 10 bar with the catalyst so prepared, to produce hydrocarbons and, optionally, oxygenates of hydrocarbons.

The temperature may be from 180° C. to 250° C., more preferably from 210° C. to 240° C. The pressure more preferably may be from 10 bar to 70 bar.

Preferably, the hydrocarbon synthesis process is a Fischer-Tropsch process, more preferably a three phase Fischer-Tropsch process, still more preferably a slurry bed Fischer-Tropsch process for producing a wax product.

The hydrocarbon synthesis process may also include a hydroprocessing step for converting the hydrocarbons and, optionally, oxygenates to liquid fuels and/or chemicals.

The present invention extends also to products produced by the hydrocarbon synthesis process of the fourth aspect of the invention.

The invention will now be described in more detail with reference to the drawings and the following non-limiting examples:

EXAMPLES

Example 1

Inventive

Figure 1:
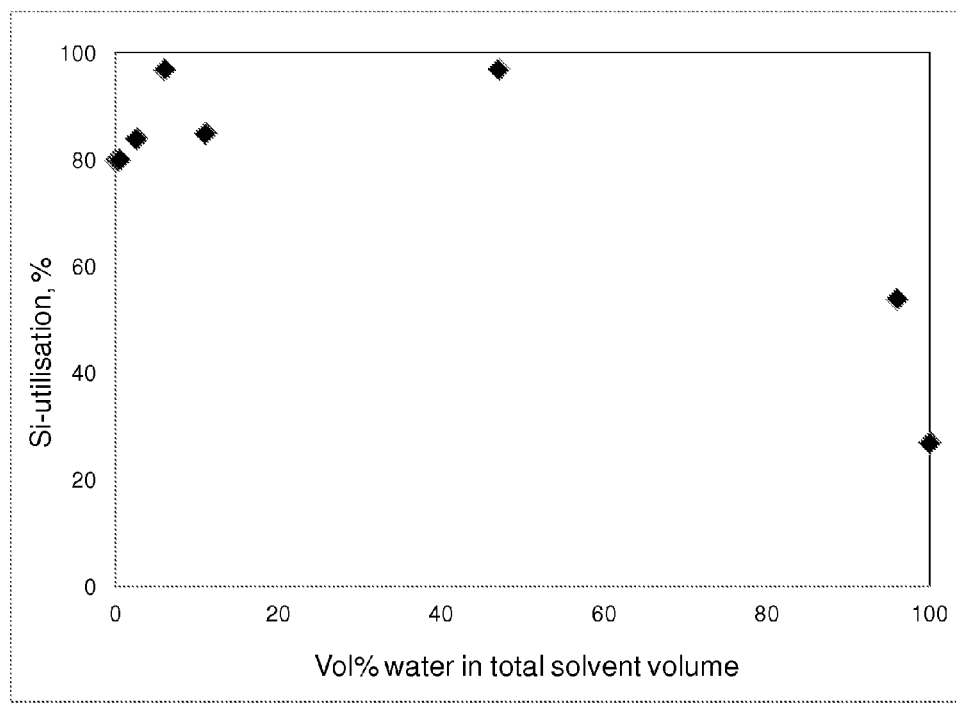
FIG. 1 shows, for Example 13, the Si-utilisation for Si modification of Puralox SCCa-2/150, as a function of the water concentration during the modification procedure.

Gamma alumina Puralox SCCa-5/150 was modified with Si, using TEOS (tetra ethoxy silane) in a mixture of water and ethanol as an impregnating liquid medium. TEOS was added to the solvent mixture of ethanol and water (see Table 1) and stirred for 10 minutes at 60° C. Puralox SCCa-5/150 (50 g) was added to this mixture and stirred for another 10 minutes at 60° C. The impregnating liquid medium was slowly removed while gradually decreasing the pressure from atmospheric pressure to 80 mbar(a) and maintaining it at 80 mbar(a) until dryness, while the temperature was maintained at 60° C. By means of calcination at 510° C. for 2 hours in air, the resultant modifying component containing catalyst support material was thus converted to a calcined modified catalyst support.

Example 2

Inventive

A modified catalyst support, as described in Example 1, was prepared, but with 2.5 vol % water in the total solvent mixture, i.e. in the impregnating liquid medium (see Table 1).

Example 3

Inventive

A modified catalyst support, as described in Example 1, was prepared, but with 6 vol % water in the total solvent mixture (see Table 1).

Example 4

Inventive

A modified catalyst support, as described in Example 1, was prepared, but with 7.5 vol % water in the total solvent mixture (see Table 1).

Example 5

Inventive

A modified catalyst support, as described in Example 1, was prepared, but with 11 vol % water in the total solvent mixture (see Table 1).

Example 6

Comparative

A modified catalyst support, as described in Example 1, was prepared, but with 17 vol % water in the total solvent mixture (see Table 1).

Example 7

Comparative

A modified catalyst support, as described in Example 1, was prepared, but with 47 vol % water in the total solvent mixture (see Table 1).

Example 8

Comparative

A modified catalyst support, as described in Example 1, was prepared, but with 96 vol % water in the total solvent mixture (see Table 1).

Example 9

Inventive

A modified catalyst support, as described in Example 1, was prepared, but with 6 vol % water in the total solvent mixture (see Table 1).

Example 10

Comparative

A modified catalyst support, as described in Example 1, was prepared, but using ethanol only as solvent (i.e. no water was used).

Example 11

Comparative

A modified catalyst support, as described in Example 1, was prepared, but using water only as solvent (i.e. no ethanol was used).

Example 12

Comparative

The gamma alumina Puralox SCCa-5/150, was not modified at all.

Example 13

The silicon content of some of the modified catalyst supports was determined by means of ICP (Inductive Coupled Plasma) analysis. The silicon utilisation was calculated by dividing the silicon content as analysed by the silicon content that was aimed for, and multiplied by 100 (see results in Table 1 and FIG. 1).

The $D_{10}$ attrition index, a single impact test, was utilized to investigate the physical strength of the silica modified supports. The $D_{10}$ attrition index is determined by using a Malvern Digisizer 2000. During analysis particles are impinged onto a steel plate and the amount of breakage gives an indication of the physical strength of the particles. ±2.5 g of sample was used for each analysis. To determine the $D_{10}$ value, two measurements are required, one at an air pressure setting of 0.15 bar and one at an air pressure setting of 3.0 bar. The $D_{10}$ attrition index value is calculated by subtracting the $D_{10}$ value at an air pressure of 3.0 bar from the $D_{10}$ value at an air pressure of 0.15 bar (see results in Table 1 and FIG. 2). The $D_{10}$ attrition index is an indication of the attrition resistance—the lower the value, the better is the attrition resistance.

TABLE 1

Si-utilisation and Delta $D_{10}$ Values of modified catalyst supports.

| Support name | EtOH (ml) | Water (vol %) | TEOS (g) | Target % Si | Si-utilisation (%)[a] | Delta $D_{10}$[b] |
|---|---|---|---|---|---|---|
| Ex 1 (inventive) | 50 | 0.4 | 8.05 | 2.1 | 80 | 2.7 |
| Ex 2 (inventive) | 50 | 2.5 | 8.05 | 2.1 | 84 | 3.1 |
| Ex 3 (inventive) | 50 | 6 | 7.2 | 1.95 | 97 | 3.2 |
| Ex 4 (inventive) | 50 | 7.5 | 8.05 | 2.1 | 83 | 3.6 |
| Ex 5 (inventive) | 50 | 11 | 8.05 | 2.1 | 85 | 4.5 |
| Ex 6 (comparative) | 50 | 17 | 8.05 | 2.1 | 78 | 6.3 |
| Ex 7 (comparative) | 26 | 47 | 7.2 | 1.95 | 97 | 6.3 |
| Ex 8 (comparative) | 5 | 96 | 7.2 | 1.95 | 54 | 8 |
| Ex 9 (inventive) | 50 | 6 | 8.05 | 2.1 | 87 | 4.5 |
| Ex 10 (comparative) | 50 | 0 | 7.2 | 1.95 | 80 | 4.2 |
| Ex 11 (comparative) | 0 | 100 | 8.05 | 2.1 | 27 | 11.2 |
| Ex 12 (comparative) | 0 | 0 | 0 | 0 | 0 | 7.5 |

[a]Determined from ICP results
[b]Error ± 1 unit

It was found that the addition of low amounts of water to the ethanol during the impregnation of TEOS onto the catalyst support material according to the present invention resulted in Si-utilisation of at least 80% and usually above the Si-utilisation of a a support with no water addition during the support modification process—see FIG. 1 and Table 1.

Furthermore, the addition of low amounts of water according to the present invention also resulted in improved Si-utilisation compared to examples where very high volumes of water (comparative Example 8 and Example 11) and not according to the present invention were used.

Figure 2:
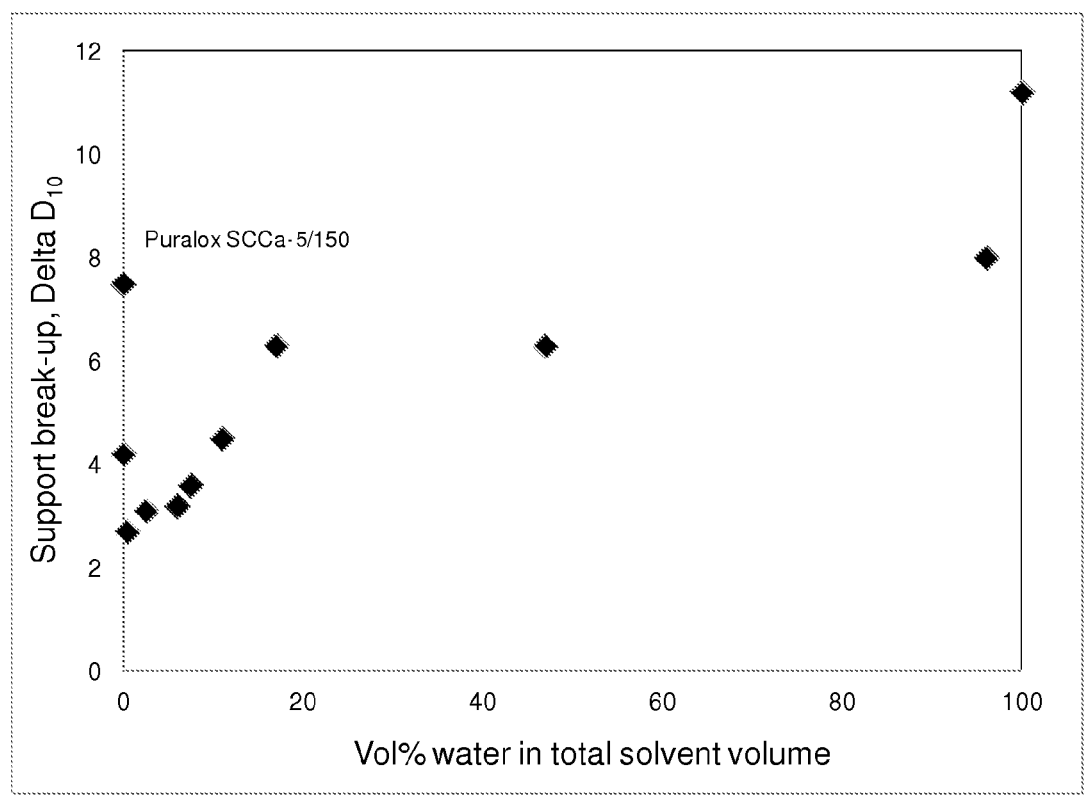
FIG. 2 depicts, for Example 13, the Delta $D_{10}$ values as a function of the water concentration during the silicon modification procedure of the Puralox SCCa-5/150.

Surprisingly, it was found that with the increased Si-utilisation, a consequence of the water addition to the support modification process, the physical strength or attrition resistance of the supports increased (despite the use of water during the modification process) as seen in the decrease in the Delta $D_{10}$ values, indicating a lower tendency for break-up of the modified catalyst support (FIG. 2).

However, the Delta $D_{10}$ values of the modified catalyst support gradually increased with higher water content in excess of 11 vol %. At a water content of 17 vol % the Delta $D_{10}$ values increased to $D_{10}$=6.3, showing no attrition resistance benefits in modifying the catalyst support material with silica, as Puralox SCCa-5/150, exhibited $D_{10}$=7.5. Thus the physical strength of the supports decreased showing higher tendency for break-up with increased water content at or above 17 vol %, as illustrated in FIG. 2. A further increase in water addition to 96% (Example 8) and using water only (Example 11) had a significant negative impact on the attrition resistance of the silica modified catalyst support, as can be seen from the high Delta $D_{10}$, at 8 and 11 respectively. In the presence of excess water two distinct phases could be observed, due to the immiscible nature of the TEOS and the water.

Example 14

Conductivity Measurements

Alumina dissolves in an aqueous medium at low pH. The dissolution of alumina results in the formation of aluminium ions. As more and more alumina dissolves, the concentration of aluminium increases with time. An increase in aluminium with time was followed by monitoring the conductivity at a constant pH of 2. The pH was kept constant by automated addition of a 10% nitric acid solution.

Figure 3:
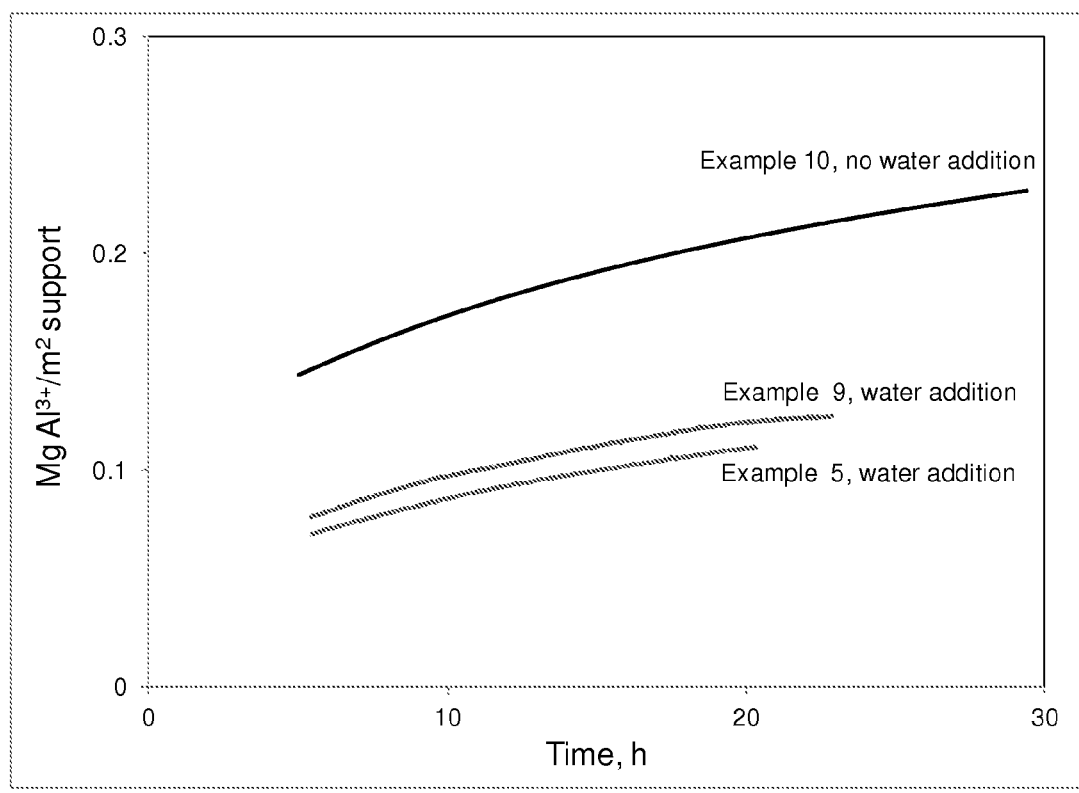
FIG. 3 shows, for Example 14, the cumulative Al dissolution as a function of time for Si modified catalyst support materials not applying water addition, as well as applying water addition.

FIG. 3 shows the cumulative Al dissolution as a function of time for Si modified catalyst support materials not applying water addition (Example 10), as well as applying water addition (Example 5 and Example 9).

It can be seen that the modified support material with no water addition, dissolved faster compared to the modified support material with the addition of water during the modification step.

Example 15

Inventive

A modified catalyst support, as described in Example 1 was prepared. The water content in the total solvent mixture was 6 vol %, while the ethanol was replaced with ethyl acetate.

Example 16

Inventive

A modified catalyst support, as described in Example 1 was prepared. The water content in the total solvent mixture was 6 vol %, while the ethanol was replaced with acetone.

Example 17

Inventive

A modified catalyst support, as described in Example 1 was prepared. The water content in the total solvent mixture was 6 vol %, while the ethanol was replaced with acetonitrile.

Example 18

Inventive $D_{10}$ attrition index values of the modified support samples with different organic solvents at 6 vol % water were determined (in the same manner as in Example 13) and are shown in Table 2.

TABLE 2

The Delta $D_{10}$ values of the modified catalyst supports prepared using different solvents.

| Support name | Solvent (50 ml) | Water (vol %) | TEOS (g) | Target % Si | Delta $D_{10}{}^a$ |
|---|---|---|---|---|---|
| Ex 3 (inventive) | Ethanol | 6 | 7.2 | 1.95 | 3.2 |
| Ex 15 (inventive) | Ethyl acetate | 6 | 7.2 | 1.95 | 4.6 |
| Ex 16 (inventive) | Acetone | 6 | 7.2 | 1.95 | 3.6 |
| Ex 17 (inventive) | Acetonitrile | 6 | 7.2 | 1.95 | 4.8 |

$^a$Error ± 1 unit

As can be seen from Table 2, the change in solvent did not significantly influence the Delta $D_{10}$ value of the modified catalyst support.

Example 19

Inventive

Puralox SCCa-5/150 was evacuated to remove air from the pores. Onto this material, Puralox SCCa-5/150 (100 g), a mixture of water (1.43 ml), ethanol (28.6 ml) and TEOS (16.1 g) was impregnated (using the incipient wetness technique), targeting 6 vol % water and Si-loading of 2%. The mixture was stirred at 60° C. for 10 minutes until a free flowing powder was obtained. The resulting material was slowly dried by gradually decreasing the pressure from atmospheric pressure to 80 mbar(a) and maintaining it at 80 mbar(a), while the temperature was maintained at 60° C. By means of calcination at 510° C. for 2 hours in air, the catalyst support material was converted to a modified catalyst support.

The Delta $D_{10}$ attrition index values of the modified support samples using slurry and incipient wetness impregnation were determined (see Table 3).

TABLE 3

The Delta $D_{10}$ values of the modified catalyst supports prepared using slurry and incipient wetness impregnation.

| Support name | Solvent (ml) | Water (vol %) | TEOS (g) | Target % Si | Delta $D_{10}{}^a$ |
|---|---|---|---|---|---|
| Ex 9 inventive (slurry impregnation) | 50 | 6 | 8.05 | 2.1 | 4.5 |
| Ex 19 Inventive (incipient wetness impregnation) | 28.6 | 6 | 8.05 | 2.1 | 4.6 |

$^a$Error ± 1 unit

The change in impregnation method did not influence the attrition resistance of the support, as indicated by the similar Delta $D_{10}$ values for the modified catalyst supports.

Example 20

According to Invention

A cobalt based Fischer-Tropsch synthesis catalyst precursor with the composition 30 gCo/0.075 gPt/100 gSupport was prepared on a modified catalyst support. The modified catalyst support was prepared as described in Example 1, with 5 vol % water in the total solvent mixture containing 1.6 wt % Si, with 90% Si-utilisation.

The catalyst precursor was prepared as follows: In a first impregnation stage, Co(NO$_3$)$_2$.6H$_2$O (39.5 g) and [Pt(NH$_4$)$_4$(NO$_3$)$_2$] (0.0248 g) were dissolved in 50 ml of distilled water. To the mixture, 50 g of the Si-modified support was added and the water was driven off by adopting the drying profile shown in Table 4. Once dry, the sample was calcined at 250° C. using a fluidised bed with a flow of air for 6 hours. Then, in a second impregnation stage, the above steps were repeated using Co(NO$_3$)$_2$.6H$_2$O (28.4 g) and [Pt(NH$_4$)$_4$(NO$_3$)$_2$] (0.0407 g) dissolved in 50 ml of distilled water, and to which 50 g of the calcined material from the first impregnation stage were added; thereafter, a similar drying profile as tabled in Table 4 below was adopted to dry the sample. The dry material was then calcined at 250° C. for another 6 hours in the same manner as for the first impregnation stage.

TABLE 4

| Pressure/mbar | Temperature/° C. | Duration/min |
|---|---|---|
| Atm | 60 | 10 |
| 260 | 60 | 30 |
| 260 | 75 | 90 |
| 260 | 85 | 60 |
| 50 | 85 | 180 |

Example 21

Comparative

A cobalt based Fischer-Tropsch synthesis catalyst precursor was prepared in the same manner as in Example 20, however, onto the modified catalyst support according to Example 10.

Example 22

Cobalt catalyst precursors of Examples 20 and 21 were reduced prior to Fischer-Tropsch synthesis in a tubular reactor at a hydrogen space velocity of 200 ml$_n$hydrogen/g$_{catalyst}$h and atmospheric pressure. The temperature was increased to 425° C. at 1° C./min, after which isothermal conditions were maintained for 16 hours.

Between 10 g and 30 g of the resultant reduced catalyst, ranging between 38 µm to 150 µm, was suspended in 300 ml molten wax and loaded in a CSTR with an internal volume of 500 ml, under a nitrogen blanket.

The pressure was increased to 18 bar and the temperature to 230° C., where after the synthesis was introduced. The synthesis feed gas consisted of hydrogen and carbon monoxide, and contained 10% argon as an internal standard. This reactor was electrically heated and sufficiently high stirrer speeds were employed so as to eliminate any gas-liquid mass transfer limitations. The feed flow was controlled by means of Brooks mass flow controllers, and space velocities ranging from 2 and 4 m$^3$$_n$/kg$_{catalyst}$h were used.

Further details about the experimental conditions for the Fischer-Tropsch synthesis process and the FT performance after 8 days on-line are presented in Table 5.

TABLE 5

The experimental conditions for the Fischer-Tropsch synthesis process and the FT performance after 8 days on-line.

| | Ex 20 (inventive) | Ex 21 (comparative) |
|---|---|---|
| Modified catalyst support | 5 vol % water, targeted 1.7 wt % Si, containing 1.6 wt % Si, 90% Si-utilisation. | No water, targeted 1.95 wt % Si, containing 1.6 wt % Si, 80% Si-utilisation |
| Time on-line (days) | 8 | 8 |
| Reactor pressure (bar) | 18.1 | 18.4 |
| Reactor temperature (° C.) | 230 | 230 |
| Clean syngas with H$_2$/CO-ratio | 1.6 | 1.6 |
| Reactor Partial Pressures (bar) | | |
| H$_2$ | 4.7 | 4.8 |
| CO | 3.9 | 4.2 |
| H$_2$O | 4.3 | 4.3 |
| Syngas conversion (%) | 61 | 60 |
| Activity (relative to example 21) | 1.0 | 1.0 |
| CH$_4$ selectivity (C-atom %) | 6.1 | 6.2 |

It can be seen from Table 5 that the Fischer-Tropsch performance of the catalyst containing the TEOS/ethanol/water modified catalyst support (Example 20) is comparable to the catalyst containing the TEOS/ethanol modified catalyst support (Example 21). Due to the increased silicon utilisation, a consequence of the water addition, the targeted TEOS was lowered, i.e. less TEOS was added, to effect similar Si loadings, which in-turn did not negatively influence FT performance of the catalyst.

In general, the examples have thus shown that support modification can be improved by using water/organic solvent mixtures with not more than 20% water, which improved the mechanical strength and the Si utilisation of the support, without affecting the FT performance.

Example 23

Comparative

Gamma alumina Puralox SCCa-150 (B31624) was modified with Ti, using Ti(O$^t$Bu)$_4$ (titanium tetrabutoxide) dissolved in a solvent mixture (impregnating liquid medium) of ethanol and 19 vol % acetic acid. Ti(O$^t$Bu)$_4$ was added to the solvent mixture (see Table 6) and stirred for 10 minutes at 60° C. Puralox SCCa-150 (B31634) was added to this mixture and stirred for another 10 minutes at 60° C. The solvent mixture was slowly removed with a gradual decrease of the pressure from atmospheric pressure to 80 mbar and maintaining it at 80 mbar until dryness, while the temperature was maintained at 60° C. By means of calcination at 550° C. for 2 hours in air, the resultant modifying component containing catalyst support material was thus converted to a calcined modified catalyst support.

Example 24

Inventive

A modified catalyst support as described in Example 23, was prepared, but with 5 vol % water in the total solvent mixture, i.e. in the impregnating liquid medium which thus comprised ethanol, acetic acid and water (see Table 6).

Example 25

Comparative

A modified catalyst support as described in Example 23, was prepared, but with TEOS (tetraethoxy silane) instead of Ti(O$^i$Bu)$_4$ as the modifying agent (see Table 6).

Example 26

Inventive

A modified catalyst support as described in Example 25, was prepared, but with 5 vol % water in the total solvent mixture, i.e. in the impregnating liquid medium which thus comprised ethanol, acetic acid and water (see Table 6).

Example 27

Comparative

A modified catalyst support as described in Example 23, was prepared, but with Zr(O$^i$Pr)$_3$ (zirconium isopropoxide) instead of Ti(O$^i$Bu)$_4$ as the modifying agent (see Table 6).

Example 28

Inventive

A modified catalyst support as described in Example 27, was prepared, but with 10 vol % water in the total solvent mixture i.e. in the impregnating liquid medium which thus comprised ethanol, acetic acid and water (see Table 6).

Example 29

Comparative

A modified catalyst support as described in Example 25, was prepared, but no post impregnation calcination step was performed (see Table 6).

Example 30

Inventive

A modified catalyst support as described in Example 29, was prepared, but with 5 vol % water in the total solvent mixture i.e. in the impregnating liquid medium which thus comprised ethanol, acetic acid and water (see Table 6).

Example 31

Comparative

Pural (boehmite phase alumina) was modified with Si, using TEOS (silicon tetraorthosilicate) in ethanol as an impregnating liquid medium. TEOS was added to the ethanol (see Table 6) and stirred for 10 minutes at 60° C. Pural was added to this mixture and stirred for another 10 minutes at 60° C. The solvent was slowly removed with a gradual decrease in the pressure from atmospheric pressure to 80 mbar and maintaining it at 80 mbar until dryness, while the temperature was maintained at 60° C. By means of calcination at 550° C. for 2 hours in air, the modifying component containing catalyst support material was thus converted to a calcined modified catalyst support (Table 6).

Example 32

Inventive

A modified catalyst support as described in Example 31, was prepared, but with 5 vol % water in a solvent mixture of ethanol and water i.e. in an impregnating liquid medium which thus comprised ethanol and water (see Table 6).

Example 33

Comparative

Pural (boehmite phase alumina) was calcined at 550° C. for 2 hours and was not modified at all.

Example 34

Comparative

Titania (spray dried and calcined at 550° C. for 2 hours) was modified with Si, using TEOS (silicon tetraorthosilicate) dissolved in ethanol. TEOS was added to the ethanol (see Table 6) and stirred for 10 minutes at 60° C. Titania was added to this mixture and stirred for another 10 minutes at 60° C. The solvent was slowly removed with a gradual decrease in the pressure from atmospheric pressure to 80 mbar and maintaining it at 80 mbar until dryness, while the temperature was maintained at 60° C. By means of calcination at 550° C. for 2 hours in air, the modifying component containing catalyst support material was thus converted to a calcined modified catalyst support (see Table 6).

Example 35

Inventive

A modified catalyst support as described in Example 34, was prepared, but with 19 vol % acetic acid and 5 vol % water in the total solvent mixture, i.e. in an impregnating liquid medium which thus comprised ethanol, acetic acid and water (see Table 6).

Example 36

Comparative

Titania (spray dried and calcined at 550° C. for 2 hours), was not modified at all.

TABLE 6

| Example | Support | Water (vol %) | Metal | Target wt % M | M-utilisation (%) | Delta $D_{10}$ (µm) |
|---|---|---|---|---|---|---|
| Ex 23 (comparative) | Al$_2$O$_3$ | 0 | Ti | 2.6 | 84 | 5.8 |
| Ex 24 (inventive) | Al$_2$O$_3$ | 5 | Ti | 2.6 | 89 | 4.0 |
| Ex 25 (comparative) | Al$_2$O$_3$ | 0 | Si | 1.6 | 70 | 3.8 |
| Ex 26 (inventive) | Al$_2$O$_3$ | 5 | Si | 1.6 | 83 | 3.2 |

TABLE 6-continued

| Example | Support | Water (vol %) | Metal | Target wt % M | M-utilisation (%) | Delta $D_{10}$ (μm) |
|---|---|---|---|---|---|---|
| Ex 27 (comparative) | $Al_2O_3$ | 0 | Zr | 2.6 | 99 | 7.5 |
| Ex 28 (inventive) | $Al_2O_3$ | 10 | Zr | 2.6 | 99 | 4.9 |
| Ex 29 (comparative) | $Al_2O_3$ | 0 | Si | 1.6 | 84 | 5.2 |
| Ex 30 (inventive) | $Al_2O_3$ | 5 | Si | 1.6 | 99 | 3.1 |
| Ex 31 (comparative) | boehmite | 0 | Si | 2.4 | 81 | 8.5 |
| Ex 32 (inventive) | boehmite | 5 | Si | 2.4 | 87 | 6.2 |
| Ex 33 (comparative) | boehmite | — | — | — | — | 10.5 |
| Ex 34 (comparative) | $TiO_2$ | 0 | Si | 1.6 | 80 | 1.5 |
| Ex 35 (inventive) | $TiO_2$ | 5 | Si | 1.6 | 92 | 1.0 |
| Ex 36 (comparative) | $TiO_2$ | — | — | — | — | 7.1 |

The metal utilization and the delta D10 values were determined in the same manner as described in Example 13

Example 37

Figure 4:
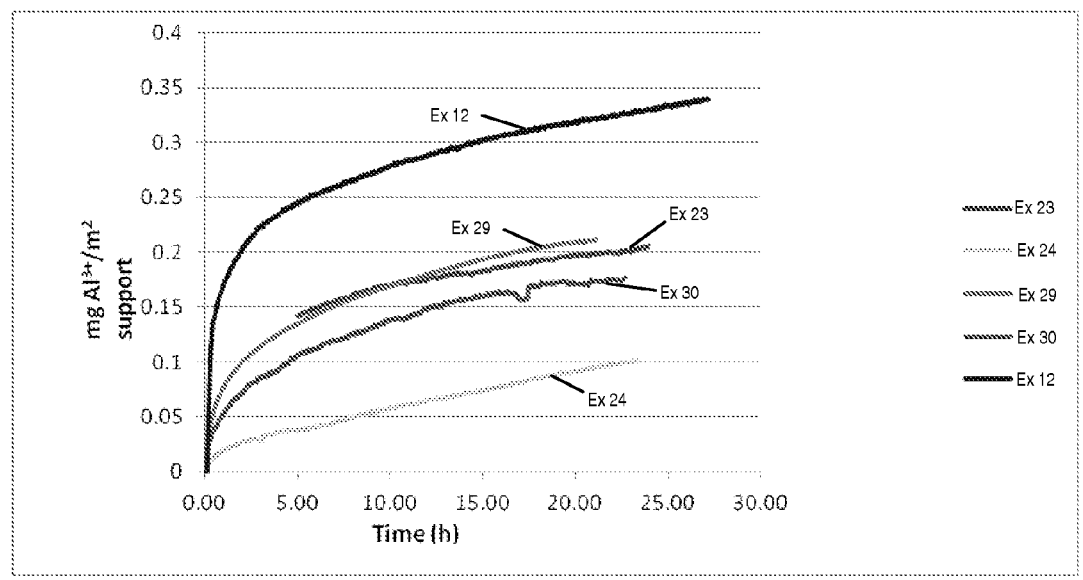
FIG. 4 shows, for Example 37, the cumulative Al dissolution as a function of time for the modified catalyst support materials of Examples, 12, 23, 24, 29 and 30.

The cumulative Al dissolution as a function of time was tested as per procedures of Example 14 for samples from Examples 12, 23, 24, 29 and 30 (see FIG. 4).

Example 38

Comparative

A cobalt catalyst precursor was prepared in the same manner as described in Example 20, except that the support of Example 23 was used.

Example 39

Inventive

A cobalt catalyst precursor was prepared in the same manner as described in Example 20, except that the support of Example 24 was used.

Example 40

Comparative

A cobalt catalyst precursor was prepared in the same manner as described in Example 20, except that the support of Example 12 was used. TEOS modification, using the procedure according to Example 25, was performed, except that no calcination at 550° C. was executed.

Example 41

Inventive

A cobalt catalyst precursor was prepared in the same manner as described in Example 20, except that the support of Example 12 was used. TEOS modification, using the procedure according to Example 26, was performed, except that no calcination at 550° C. was executed.

TABLE 7

| Example | Support | Water (vol %) used during support modification | Metal used for support modification | Target wt % of support modifying metal | Delta $D_{10}$ of catalyst (μm) | Al leaching (ppm) |
|---|---|---|---|---|---|---|
| Ex 38 (comparative) | $Al_2O_3$ | 0 | Ti | 2.6 | 4.7 | 89 |
| Ex 39 (inventive) | $Al_2O_3$ | 5 | Ti | 2.6 | 3.0 | 11 |
| Ex 40 (comparative) | $Al_2O_3$ | 0 | Si | 1.6 | 4.6 | 58 |
| Ex 41 (inventive) | $Al_2O_3$ | 5 | Si | 1.6 | 3.0 | 19 |

The invention claimed is:

1. A method of preparing a modified catalyst support, the method comprising:
   contacting a catalyst support material with a modifying component precursor in an impregnating liquid medium wherein the impregnating liquid medium comprises a mixture of water and an organic liquid solvent for the modifying component precursor, which mixture contains at least 2.5% by volume water, but less than 12% by volume water based on the total volume of the impregnating liquid medium, the catalyst support material is selected from the group consisting of a catalyst support precursor which is convertible to a catalyst support upon calcination thereof, the catalyst support being in the form of a metal oxide which is an oxide of a metal selected from the group consisting of Al, Si, Ti, Mg, Zr and Zn; and a catalyst support selected from the group consisting of alumina in the form of one or more aluminium oxides, silica ($SiO_2$), titania ($TiO_2$), magnesia (MgO), zirconium oxide ($ZrO_2$), zinc oxide (ZnO) and mixtures thereof; and the modifying component precursor comprises a compound of a modifying component selected from the group consisting of Si, Zr, Ti, Cu, Zn, Mn, Ba, Ni, Al, V, W, La and mixtures of two or more thereof, thereby to obtain a modifying component containing catalyst support material; and
   optionally, calcining the modifying component containing catalyst support material at a temperature above 100° C. to obtain a modified catalyst support.

2. The method according to claim 1 wherein the impregnating liquid medium contains not more than 10% by volume water.

3. The method according to claim 1, wherein the organic liquid solvent comprises a liquid organic compound which includes at least one heteroatom selected from oxygen or nitrogen.

4. The method according to claim 3, wherein the heteroatom of the liquid organic compound of the organic liquid solvent is oxygen, with the oxygen containing liquid organic compound being an alcohol.

5. The method according to claim 4 wherein the liquid organic compound of the organic liquid solvent is ethanol.

6. The method according to claim 3 wherein the heteroatom of the liquid organic compound of the organic liquid solvent is nitrogen, with the nitrogen containing liquid organic compound being acetonitrile.

7. The method according to claim 3 wherein the organic liquid solvent comprises a mixture of liquid organic compounds.

8. The method according to claim 1, wherein the modifying component precursor includes one or more organic groups bound to the modifying component.

9. The method according to claim 1 wherein, by contacting the catalyst support material with the modifying component precursor in the impregnating liquid medium, the modifying component precursor is thus introduced into and/or onto the catalyst support material by means of impregnation.

\* \* \* \* \*